United States Patent [19]
Crombie

[11] Patent Number: 5,961,524
[45] Date of Patent: Oct. 5, 1999

[54] SCREW AND METHOD OF ATTACHMENT TO A SUBSTRATE

[75] Inventor: John S. Crombie, East Hanover, N.J.

[73] Assignee: Stryker Technologies Corporation, Kalamazoo, Mich.

[21] Appl. No.: 09/038,314

[22] Filed: Mar. 11, 1998

[51] Int. Cl.⁶ .................................................. A61B 17/58
[52] U.S. Cl. ........................... 606/104; 606/105; 606/73; 606/72; 606/65
[58] Field of Search ................................... 606/104, 105, 606/61, 62, 63, 73, 72, 65

[56] References Cited

U.S. PATENT DOCUMENTS

| | | | |
|---|---|---|---|
| 4,290,756 | 9/1981 | Sellers | 433/225 |
| 5,454,811 | 10/1995 | Huebner | 606/60 |

*Primary Examiner*—Michael Buiz
*Assistant Examiner*—Tan-Uyen T. Ho
*Attorney, Agent, or Firm*—Lerner, David, Littenberg, Krumholz & Mentlik, LLP

[57] ABSTRACT

A method of implanting a threaded tapered screw into a substrate having a hardness less than the hardness of the screw comprises: (a) drilling a pilot hole with a drill having substantially the same taper as the taper of the tapered screw, so as to provide a pilot hole having no threads therein; (b) inserting the tapered screw into the pilot hole (preferably by merely dropping the screw into the pilot hole); and then (c) further advancing the tapered threaded screw into the pilot hole. The method requires only a minimal amount of strength to insert the screw into the hole, is preferably used to secure a bioabsorbable screw within bone, is very quickly and efficiently done without any extra step of tapping or cutting threads within the hole, invades or disrupts the bone structure only minimally, and requires no screw-holding forceps for stabilizing the screw. The tapered threaded bioabsorbable screw is self-centering and self-aligning and is itself a novel tapered screw especially suitable for use in orthopedics for implantation into bone. The screw has a taper and preferably has threads having rounded crests, has a slot for ease of insertion, has a single thread pitch, and is bioabsorbable.

16 Claims, 1 Drawing Sheet

SCREW AND METHOD OF ATTACHMENT TO A SUBSTRATE

BACKGROUND OF THE INVENTION

This invention relates generally to screws and attachment to a substrate and relates more particularly to bioabsorbable screws and their attachment to bone.

DESCRIPTION OF THE PRIOR ART

In the prior art, in inserting screws into substrates, generally (with metal screws or with other prior art screws), a pilot hole is drilled, and then a metal tap is used for cutting threads into the substrate. Alternatively, the screw itself can be self-tapping, producing threads in the substrate itself generally by cutting the threads into the substrate.

In the important area in orthopedics in which bioabsorbable screws are used, the bioabsorbable materials generally have low torsional strength. This necessitates, as disclosed for example in U.S. Pat. No. 5,593,410 to Vrespa, "Screw Device for Fixing Prostheses to Bones", issued Jan. 14, 1997, threads must be formed in the bone before the screw is inserted. Additionally, as disclosed for example in the article entitled "A Bioabsorbable Poly-L-Lactide Miniplate and Screw System for Osteosynthesis in Oral and Maxillofacial Surgery," K. BESSHO, et al., J. Oral Maxillofac. Surg., 55:941–945, 1997, on page 946, "For the foreseeable future, insertion of polymer screws (which, unlike metals, are softer than bone) will require pre-cutting (tapping) of the threads. This single step serves as the greatest difference from placing metal fixation." However, this procedure involves an extra step of forming threads in the bone before screw insertion.

A more desirable method is for the screw to form its own threads and thus be self-tapping, as is widely known in the use of metal screws.

However, due to weakness of the bioabsorbable materials, if the bioabsorbable screw is self-tapping, it must have of necessity a very low frictional fit with the bone or limited thread engagement.

If the screw is self-tapping, a large number of voids are formed around the screw as the tapping procedure takes place in order to prevent breakage, thus allowing the screw to have clearance in order to pass through the substrate with little friction.

It is desirable in inserting screws into bone to have minimal invasion of the bone, so that the bone structure is not disrupted. Additionally, it is desirable to have the bone screw be strongest just under the head of the screw, where screws commonly fail.

If the frictional forces become too great as the thread is passed into the bone, the screw experiences torsional failure before the screw is fully inserted. In order to overcome this problem, the length of the bioabsorbable screws had to be limited.

Generally in the prior art, for a given screw length, each full thread on the shaft requires one full turn for full insertion of the screw.

Bioabsorbable material is stronger in compression than in torsion. It is desirable to rely on compression, rather than on torsion in using bioabsorbable materials so as to be able to apply more force to the screw.

An object of this invention is a method of inserting a screw which will provide bone contact along the full length of the screw upon insertion of the screw into the bone.

Another object of this invention is a bioabsorbable screw which need not be limited in screw length.

A further object of this invention is a bioabsorbable screw and a method of inserting that bioabsorbable screw into bone in a very efficient way such that very little time is used and very little force is used in inserting and locking the bioabsorbable screw into bone.

Yet another object of this invention is a method of securing a tapered threaded screw made of a material having a first hardness, the screw having threads and having a taper angle $\alpha$, into a substrate having a second hardness which is less than the first hardness by use of a very low insertion force.

Another object of this invention is a method of securing a tapered threaded screw within a substrate such that the number of rotations required to insert the screw is limited as much as possible and thus the time required for insertion is also minimal.

Another object of this invention is a method of securing a tapered screw such that a press-fit or interference fit between the screw and the substrate arises.

Another object of this invention is a method of securing a bone screw within bone such that minimal invasion of the bone structure results.

Yet another object of this invention is a method of securing a tapered threaded screw within a bone in which no screw-holding forceps are needed to stabilize the screws.

A further object of this invention is a self-centering, self-aligning bioabsorbable screw which minimizes any problems with alignment and problems of crossing threads and mismatching of threads within a threaded hole.

Yet another object of this invention is a method of securing a tapered threaded screw within a substrate, such that the threads of the screw will not be stripped.

SUMMARY OF THE INVENTION

These and other objects are satisfied by the method of the invention of securing a tapered threaded screw having threads and having a taper angle $\alpha$ and being formed from a material having a first hardness within a substrate having a second hardness which is less than the first hardness by use of a very low insertion force, the method comprising: (1) drilling a hole within the substrate by use of a tapered drill having a taper angle substantially equal to the taper angle $\alpha$ of the tapered threaded screw, so as to form a tapered unthreaded pilot hole; (2) inserting the tapered threaded screw into the tapered unthreaded pilot hole so that the threads of the screw just minimally contact the pilot hole, so as to provide maximum congruence between the pilot hole and the screw; and then (3) turning the screw through only a very small angle $\beta$ so that the screw advances into the substrate and the threads compress and deform the substrate at the places where the threads contact the substrate, thereby locking the screw within the substrate.

A press-fit or interference fit between the tapered threaded screw and the unthreaded tapered hole arises in which bone is displaced so as to make room for the threads of the screw. By use of a tapered drill, a tapered unthreaded pilot hole is formed; and the tapered threaded screw, upon insertion into and locking within the pilot hole deforms the substrate due to its greater hardness, as compared with the hardness of the substrate. No step of tapping the pilot hole is required due to the specially produced maximum congruence between the pilot hole and the screw. Therefore, a very fast and efficient method of securing the screw within the substrate is provided.

Additionally, according to the invention, in a preferred aspect of the invention, the screw is made of a bioabsorbable material and the screw is inserted into bone.

In yet another aspect of the invention, in a preferred embodiment, a novel bioabsorbable screw is provided, the screw having a particular taper and having threads which have rounded crests, as opposed to having crests which are sharp cutting edges.

DESCRIPTION OF THE PREFERRED EMBODIMENTS

DETAILED DESCRIPTION OF THE DRAWING

Figure 1:
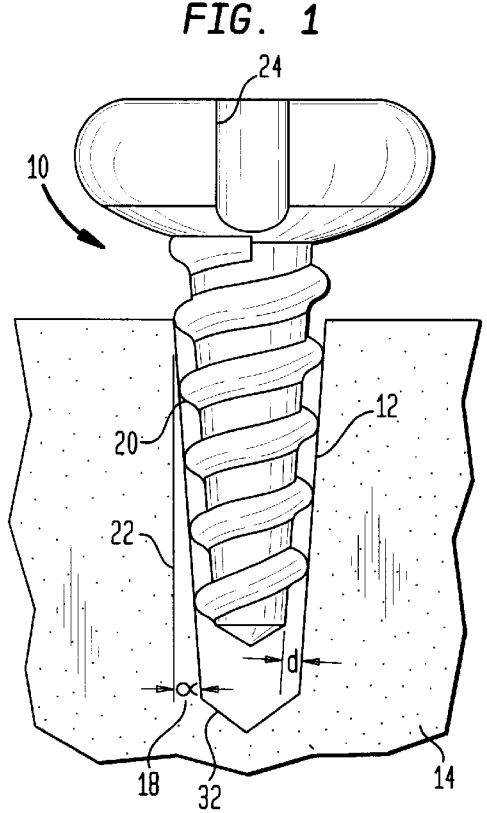
FIG. 1 is a view, partially in cross-section, showing a tapered screw just after it has been dropped into a tapered unthreaded hole which was previously cut into a substrate which is bone, just prior to seating of the screw.

Referring to the drawing, in FIG. 1, a tapered screw of the invention is shown partially in cross-section in a preferred embodiment in which the screw is made of a bioabsorbable material and the material into which the screw is being inserted is bone.

The tapered screw referred to generally as (10) is shown in FIG. 1 just after being dropped into a tapered unthreaded hole (referred to generally as (12) which was previously formed within the substrate (14), which in a preferred embodiment is bone. The tapered hole was previously formed within substrate (14) by a tapered drill bit (16) shown in detail in FIG. 3.

The taper of angle $\alpha$ 18 of the tapered threaded screw (10), the taper angle of the tapered unthreaded hole (12), and the taper angle of the tapered drill (16) are all substantially equal.

Tapered threaded screw (10) is formed of a material which has a hardness which is greater than that of the substrate (14) into which the tapered threaded screw (10) is intended to be inserted. In a preferred embodiment, the screw (10) is made of a bioabsorbable material and the substrate (14) is bone.

Tapered threaded screw (10) has threads (20) which have crests (22) which are preferably rounded crests, as opposed to crests which are sharp cutting edges. Screw (10) also has a slot (24), into which an insertion device (not shown) can be placed, in order to be able to easily insert the screw (10) into the substrate (14). The bone portion (26) adjacent to the crests is shown compressed and deformed.

Figure 2:
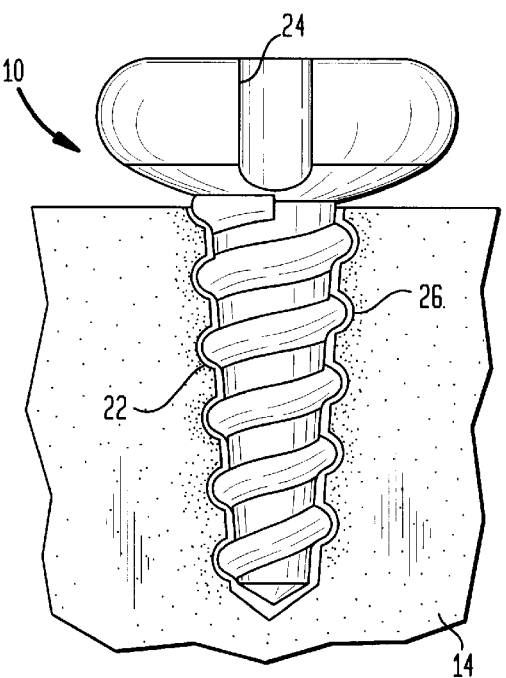
FIG. 2 is a view of the tapered screw of FIG. 1, after it has been seated in the substrate bone.

In FIG. 2, the tapered screw (10) is shown in its locked or seated position within substrate (14), which is bone in a preferred embodiment. Crests (22) have compressed and displaced the bone(14) when tapered screw (10) is locked into position. Locking is easily accomplished by turning threaded screw (10) through only a very small angle $\beta$.

Figure 3:
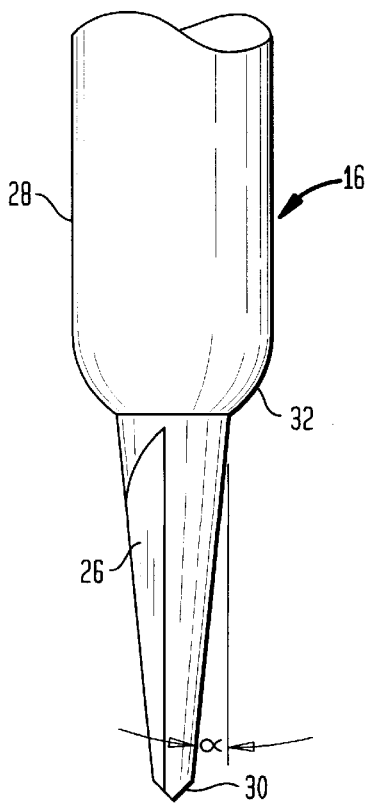
FIG. 3 is a schematic illustration of a tapered drill bit which is especially useful for forming an unthreaded hole in a substrate.

In FIG. 3, a preferred embodiment of a tapered drill bit 16 is shown and has a flute 26 and a stop 28. The tip 30 or the drill bit 16 substantially matches the tip 32 of the screw 10 (shown in FIG. 1). The curvature 32 of the stop 28 (shown in FIG. 3) matches the curvature 34 under the head 36 of the screw 10 (shown in FIG. 1).

The bioabsorbable material can be any suitable biocompatible polymer material which degrades over time. An example of a preferred material is a polylactic acid (PLA) compound. Generally, when the substrate is bone, the hardness of the screw material will need to be higher than the hardness of bone.

The taper angle $\alpha$ will generally be chosen so that $2\alpha$ is within the range from about 1° to less than 90°. Preferably $2\alpha$ is within the range from about 1° to about 45° and most preferably $2\alpha$ will be within the range from about 5° to about 15°.

The angle of rotation $\beta$ of the tapered screw will depend upon the angle $\alpha$ chosen and upon the pitch chosen. The larger that angle $\alpha$ is chosen, the smaller angle $\beta$ will be.

Because the tapered screw has maximum contact with the inner surface of the tapered hole in the practice of the invention, $\beta$ will be generally small and less than 720° (i.e., two complete rotations).

Figure 4:
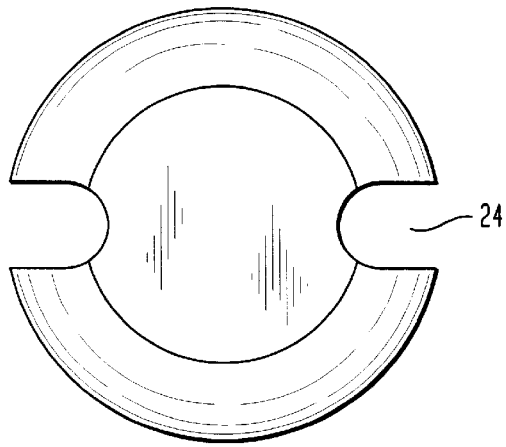
FIG. 4 is a top view of the tapered screw shown in FIGS. 1 and 2.

Provision of a slot 24 (for example as shown in FIG. 4) in the screw allows a large force to be applied to a low strength screw material. Additionally, preferably the amount of material adjacent to the screw head will be maximized and the thread depth d (also called the thread purchase) (shown in FIG. 1) will be constant.

In the practice of the invention, the tapered threaded screw will centralize itself when it is inserted into the tapered unthreaded hole. Thus, the screw will be self-aligning and self-directing.

Preferably, the screw will have a single pitch and will have rounded crests on the threads. However, the screw could have more than one pitch and could have sharp crests on the threads and still fall within the scope of the invention. Sharp crests on the threads would be more likely to break than rounded crests, but they could conceivably be used, for example when the screw is to be inserted into a soft material such as osteoporotic bone.

In the practice of the invention, the material from which the screw is formed should be either (a) harder than the substrate material or (b) less deformable (i.e., less displaceable) than the substrate material, either locally or generally within the substrate material.

The invention is not to be limited to the specific embodiments described.

I claim:

1. A method of securing a tapered threaded screw having threads with rounded crests for compressing a substrate and having a taper angle $\alpha$ and being formed from a material having a first hardness $H_1$ within a substrate having a second hardness $H_2$ which is less than said first hardness $H_1$ by use of a very low insertion force, said method comprising:

(a) drilling a pilot hole within said substrate by use of a tapered drill having a taper angle substantially equal to said angle $\alpha$ of said tapered screw, so as to form a tapered unthreaded pilot hole;

(b) then inserting said tapered threaded screw into said tapered unthreaded pilot hole so that said threads of said screw only minimally contact said pilot hole so as to provide maximum congruence between said pilot hole and said screw; and then (c) turning said screw through only a very small angle $\beta$ so that said screw advances into said substrate and said threads compress and deform said substrate at places where said threads contact said substrate, thereby locking said screw within said substrate.

2. A method according to claim 1, wherein said method includes no step of cutting of threads by use of a tapper or by use of a self-tapping screw.

3. A method according to claim 2, wherein said screw is made of a bioabsorbable material.

4. A method according to claim 3, wherein said threads of said tapered screw have rounded crests, as opposed to having crests which are sharp cutting edges and wherein 2 times said taper angle $\alpha$ is within the range from about 1° to about 45°.

5. A method according to claim 4 wherein said tapered screw is inserted by being merely dropped into said pilot hole and wherein two times said angle $\alpha$ is within the range from about 5° to about 15°.

6. A tapered screw having a taper angle $\alpha$ which is within the range from about 1 to about 45 degrees, having threads which have rounded crests, as opposed to having crests which are sharp cutting edges, having a single thread pitch, and having a slot for insertion of said screw.

7. A tapered screw according to claim 6, wherein said screw is bioabsorbable and is part of a suture anchor and, wherein $2\alpha$ is within the range from about 5° to about 15°.

8. A method of securing a screw made of a screw material which has a low torsional strength (as compared with the torsional strength of metal) into a substrate material having a yield strength (or ultimate strength) which is higher than the yield strength of said screw material, without tapping said substrate material, said screw having threads with rounded crests for compressing a substrate, said method comprising:

(a) drilling a hole within said substrate by use of a tapered drill having a taper angle equal to said angle $\alpha$, so as to form a tapered unthreaded pilot hole;

(b) inserting said tapered threaded screw into said tapered unthreaded pilot hole so that said threads of said screw only minimally contact said pilot hole, so as to provide maximum congruence between said pilot hole and said screw; and (c) turning said screw through only a very small angle $\beta$ so that said screw advances into said substrate material and said threads compress and deform said substrate material at places where said threads contact said substrate, thereby locking said screw within said substrate material.

9. A method according to claim 8, wherein said screw material is bioabsorbable.

10. A method of repairing bone fragments by use of a self-centering and self-aligning screw, said method comprising securing a screw made of a screw material which has a low torsional strength as compared with the torsional strength of metal into a substrate material having a yield strength (or ultimate strength) which is higher than the yield strength of said screw material, without tapping said substrate material, said screw having threads with rounded crests for compressing a substrate, said method comprising:

(a) drilling a hole within said substrate material by use of a tapered drill having a taper angle equal to said angle $\alpha$, so as to form a tapered unthreaded pilot hole;

(b) inserting said tapered threaded screw into said tapered unthreaded pilot hole so that said threads of said screw only minimally contact said pilot hole, so as to provide maximum congruence between said pilot hole and said screw; and (c) turning said screw through only a very small angle $\beta$ so that said screw advances into said substrate material and said threads compress and deform said substrate material at places where said threads contact said substrate material, thereby locking said screw within said substrate material.

11. A method of inserting and locking a bioabsorbable screw having a low torsional strength into a substrate material having a yield strength which is higher than the yield strength of said screw material by using only a minimal angle $\beta$ of rotation of the screw, said screw having threads with rounded crests for compressing a substrate, said method comprising:

(a) drilling a hole within said substrate material by use of a tapered drill having a taper angle equal to said angle $\alpha$, so as to form a tapered unthreaded pilot hole;

(b) inserting said tapered threaded screw into said tapered unthreaded pilot hole so that said threads of said screw only minimally contact said pilot hole, so as to provide maximum congruence between said pilot hole and said screw; and (c) turning said screw through only a very small angle $\beta$ so that said screw advances into said substrate material and said threads compress and deform said substrate material at places where said threads contact said substrate material, thereby locking said screw within said substrate material.

12. A method of using a plastic, bioabsorbable, tapered screw having a taper angle $\alpha$ and a single thread pitch such that said screw is very quickly and very easily insertable and then very quickly and very securely lockable into place within a bone, said screw having threads with rounded crests for compressing a substrate, said method comprising:

(a) drilling an unthreaded tapered hole with a tapered drill within said bone, said unthreaded tapered hole being tapered with a single taper at said taper angle $\alpha$ (of said tapered screw); and (b) inserting said tapered screw within said unthreaded tapered hole such that substantially all threads of said screw contact said unthreaded tapered hole and turning said screw through an angle of at most 720°, thus fully seating and locking said screw, with substantially all threads of said screw pushing into and deforming said bone, rather than cutting said bone, and with said threads being under compression, rather than under torsion.

13. A method according to claim 12, wherein said angle $\alpha$ is between about 1° and about 45°.

14. A method according to claim 13, wherein said screw is a part of a suture anchor.

15. A method according to claim 14, wherein said screw is an interference screw (which can hold additional material in place) or a lag screw.

16. A method according to claim 12, wherein said tapered screw has a slot and wherein said tapered screw is inserted by placing an insertion device within said slot and then turning the insertion device.

* * * * *